US012564364B2

(12) United States Patent
Akiyama et al.

(10) Patent No.: US 12,564,364 B2
(45) Date of Patent: Mar. 3, 2026

(54) X-RAY DIAGNOSTIC APPARATUS

(71) Applicant: Canon Medical Systems Corporation, Otawara (JP)

(72) Inventors: Masaki Akiyama, Nasushiobara (JP); Shumpei Ohashi, Otawara (JP); Hiroshi Yoshida, Yaita (JP); Kensei Narahara, Nasushiobara (JP); Masashi Hirasawa, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 212 days.

(21) Appl. No.: 18/473,382

(22) Filed: Sep. 25, 2023

(65) Prior Publication Data
US 2024/0099679 A1 Mar. 28, 2024

(30) Foreign Application Priority Data

Sep. 26, 2022 (JP) ................................. 2022-152888

(51) Int. Cl.
*A61B 6/00* (2024.01)
*A61B 6/04* (2006.01)

(52) U.S. Cl.
CPC .......... *A61B 6/4441* (2013.01); *A61B 6/0407* (2013.01)

(58) Field of Classification Search
CPC ... A61B 6/4441; A61B 6/0407; A61B 6/4464; A61B 6/44; A61B 8/4494
See application file for complete search history.

(56) References Cited

U.S. PATENT DOCUMENTS

| | | | | |
|---|---|---|---|---|
| 5,436,461 | A * | 7/1995 | Saffer | F16L 3/015 378/197 |
| 6,132,093 | A * | 10/2000 | Michioka | F16C 33/3825 384/45 |
| 2006/0153340 | A1* | 7/2006 | Engstrom | A61B 6/4441 378/197 |
| 2013/0148783 | A1* | 6/2013 | Ikawa | F16M 11/18 378/189 |
| 2018/0216394 | A1* | 8/2018 | Mareaux | E05F 15/643 |

FOREIGN PATENT DOCUMENTS

JP 2000-153911 A 6/2000

* cited by examiner

*Primary Examiner* — David J Makiya
*Assistant Examiner* — Mamadou Faye
(74) *Attorney, Agent, or Firm* — Oblon, McClelland, Maier & Neustadt, L.L.P.

(57) ABSTRACT

According to one embodiment, an X-ray diagnostic apparatus comprising: an arm, a pair of grooved portions, a plurality of rollers, and a plurality of belts. The arm is configured to support an X-ray tube at one end and an X-ray detector at another end and has a shape of an arc. The grooved portions are formed on side surfaces of the arm. The plurality of rollers are configured to run in the grooved portions and slidably support the arm along the arc. Each of the belts passes over at least two of the rollers and at least partially abuts on inner walls of the grooved portions.

14 Claims, 14 Drawing Sheets

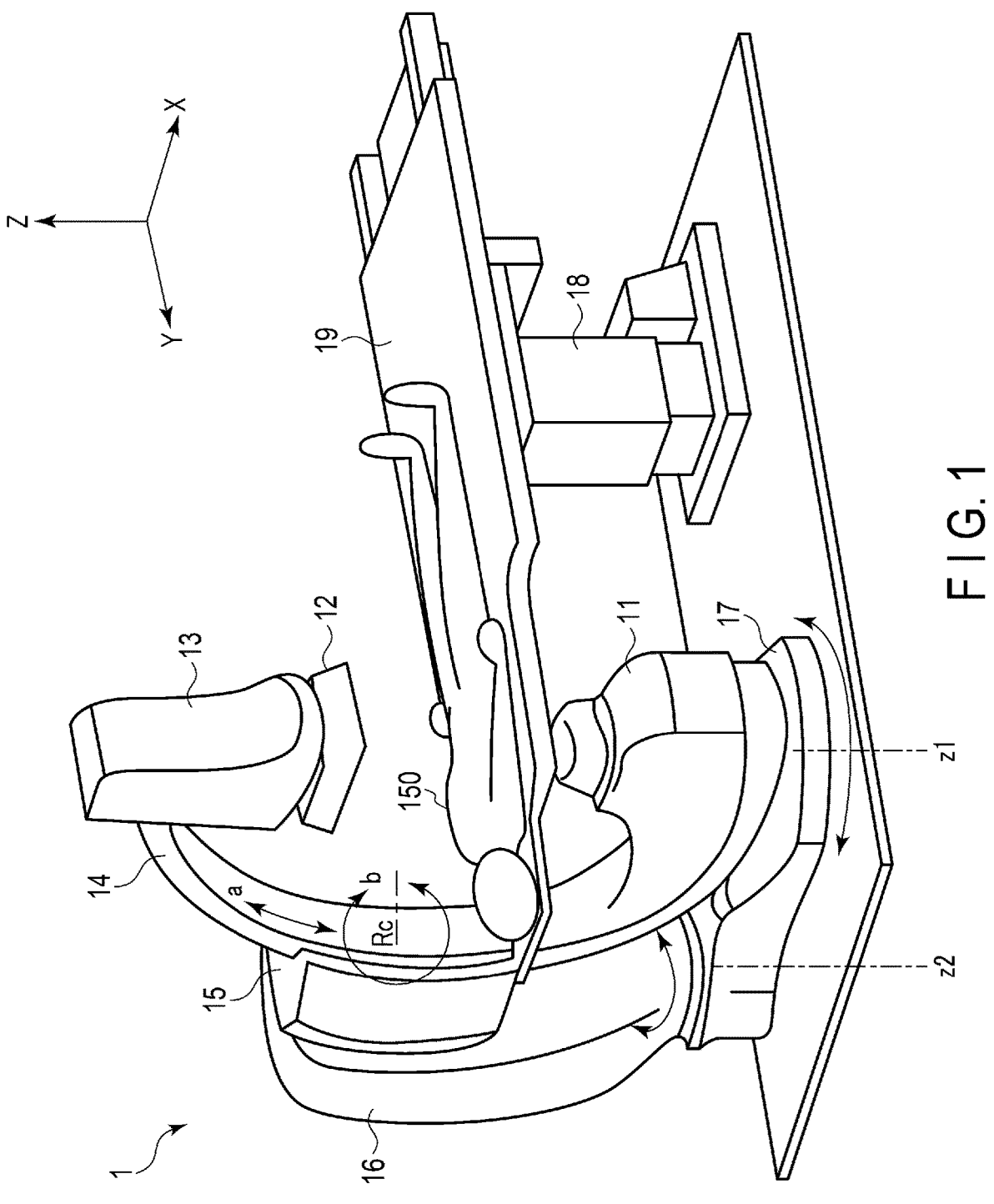
F I G. 1

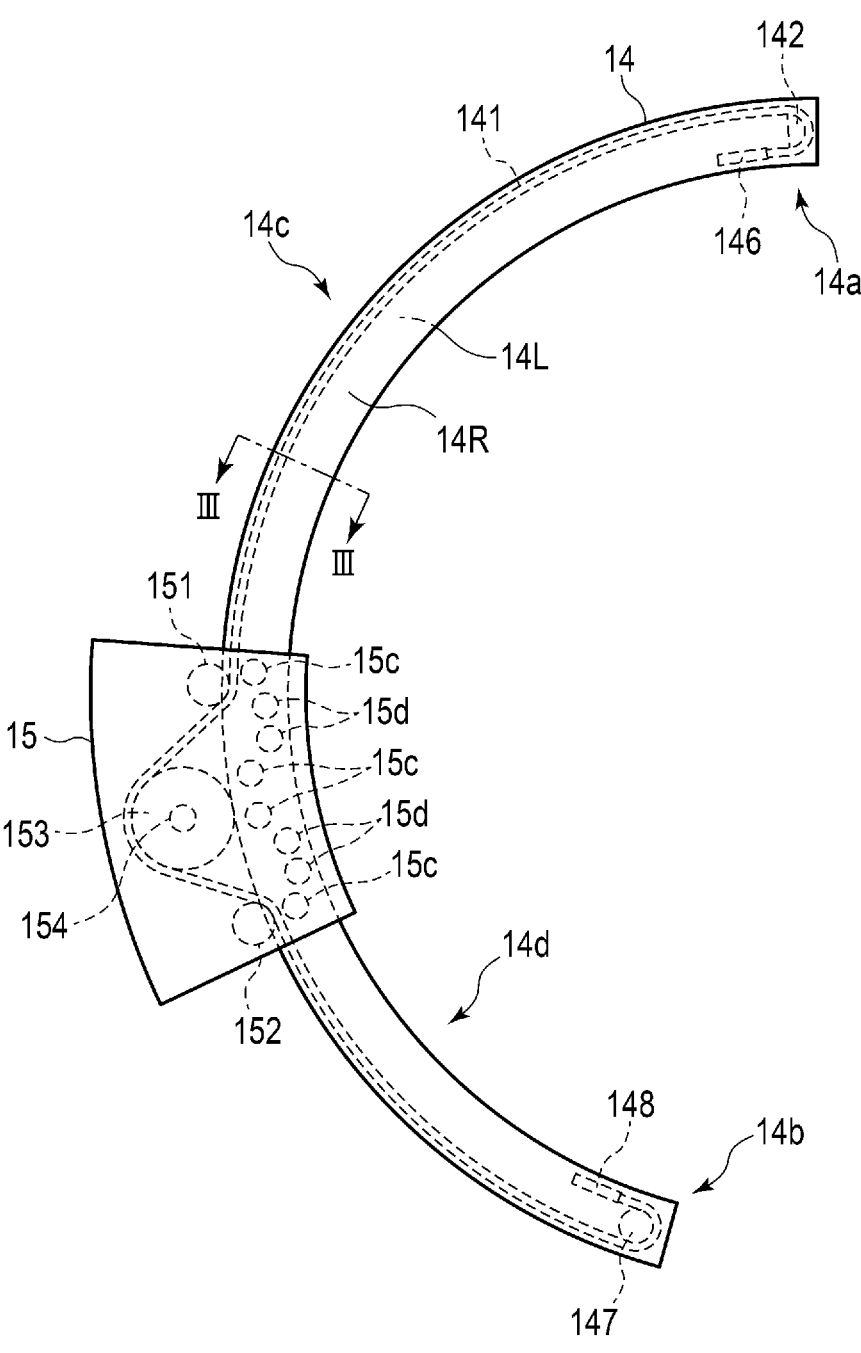
F I G. 2

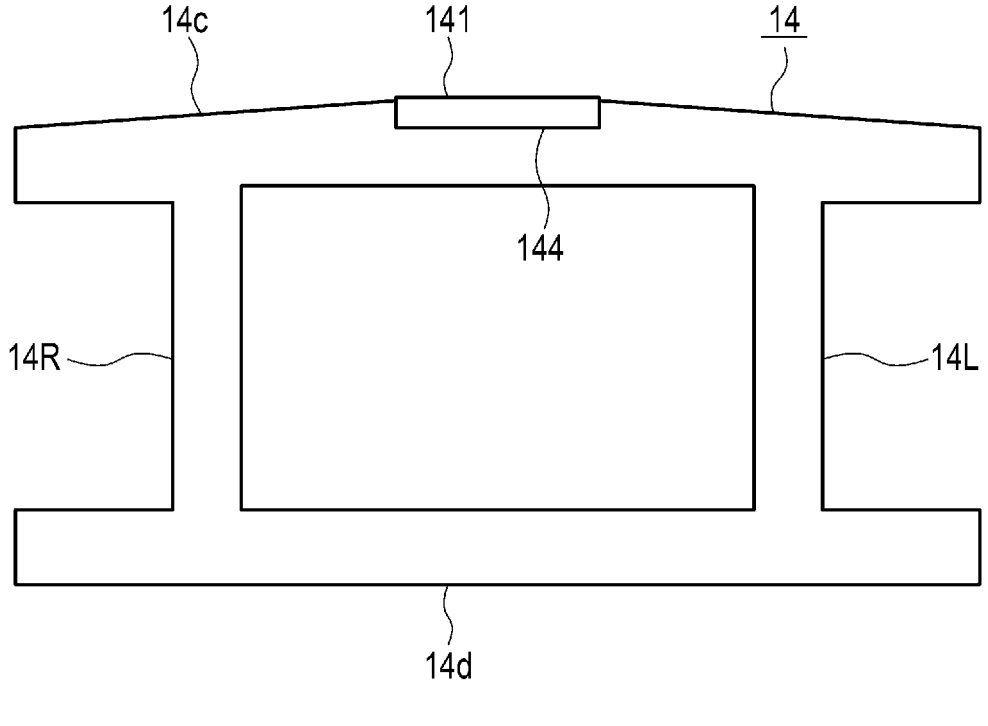
F I G. 3

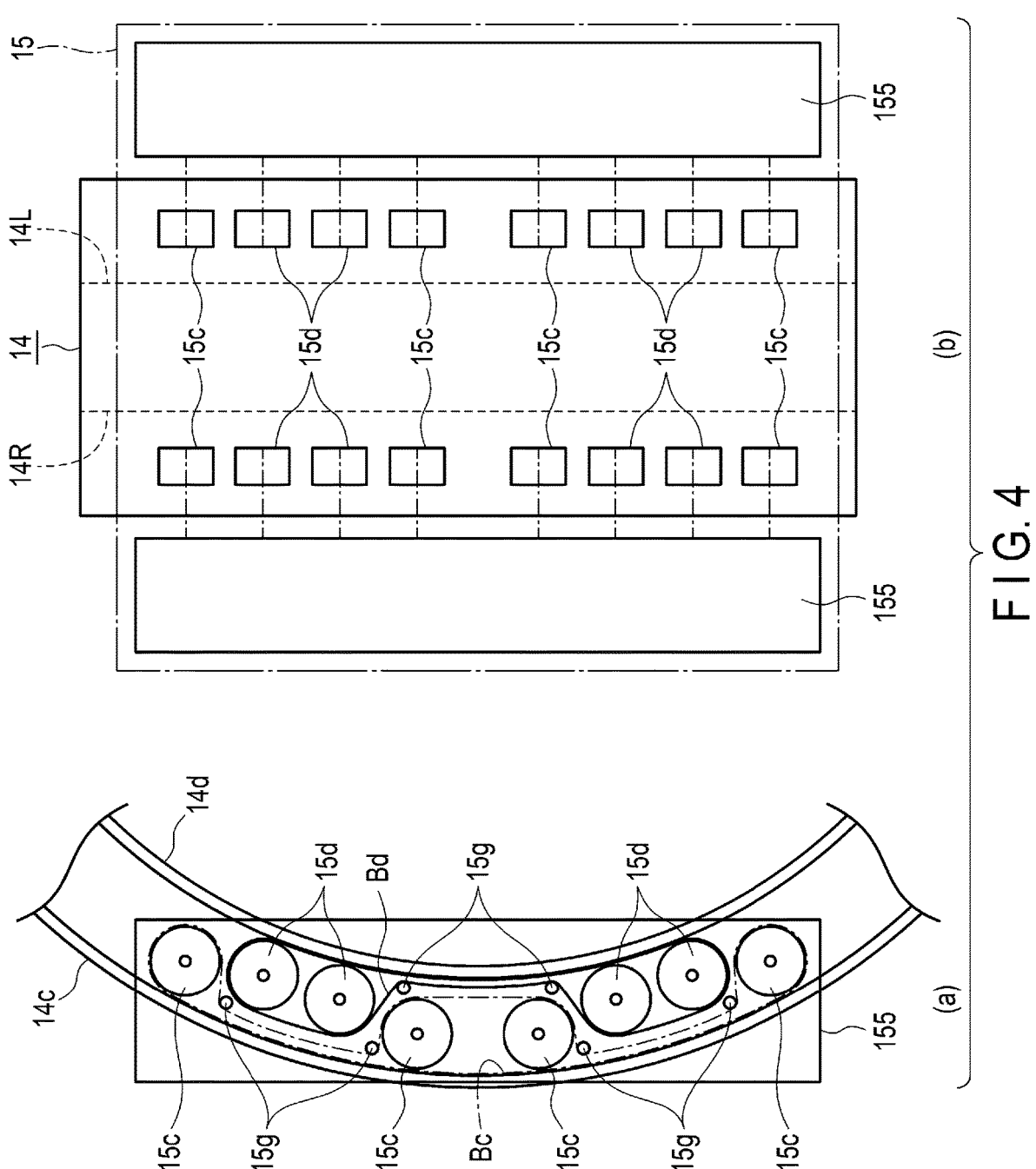
F I G. 4

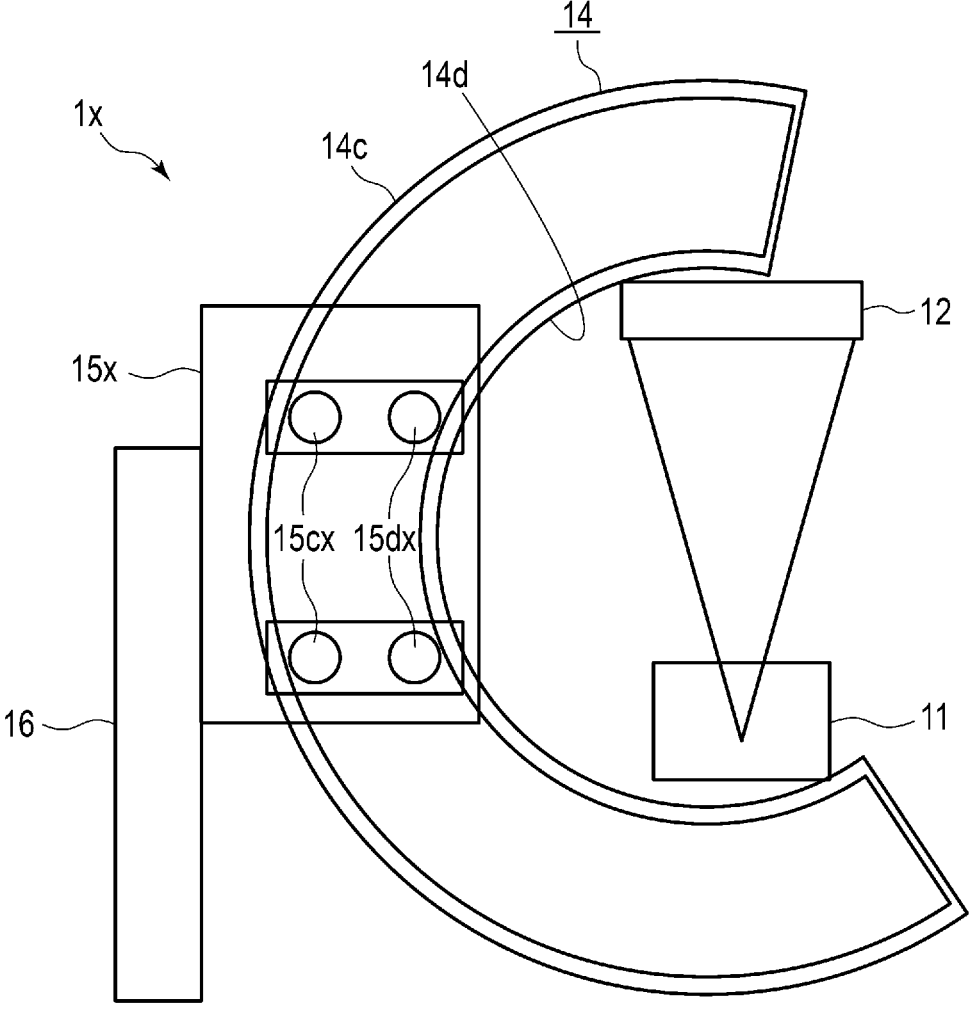
F I G . 5

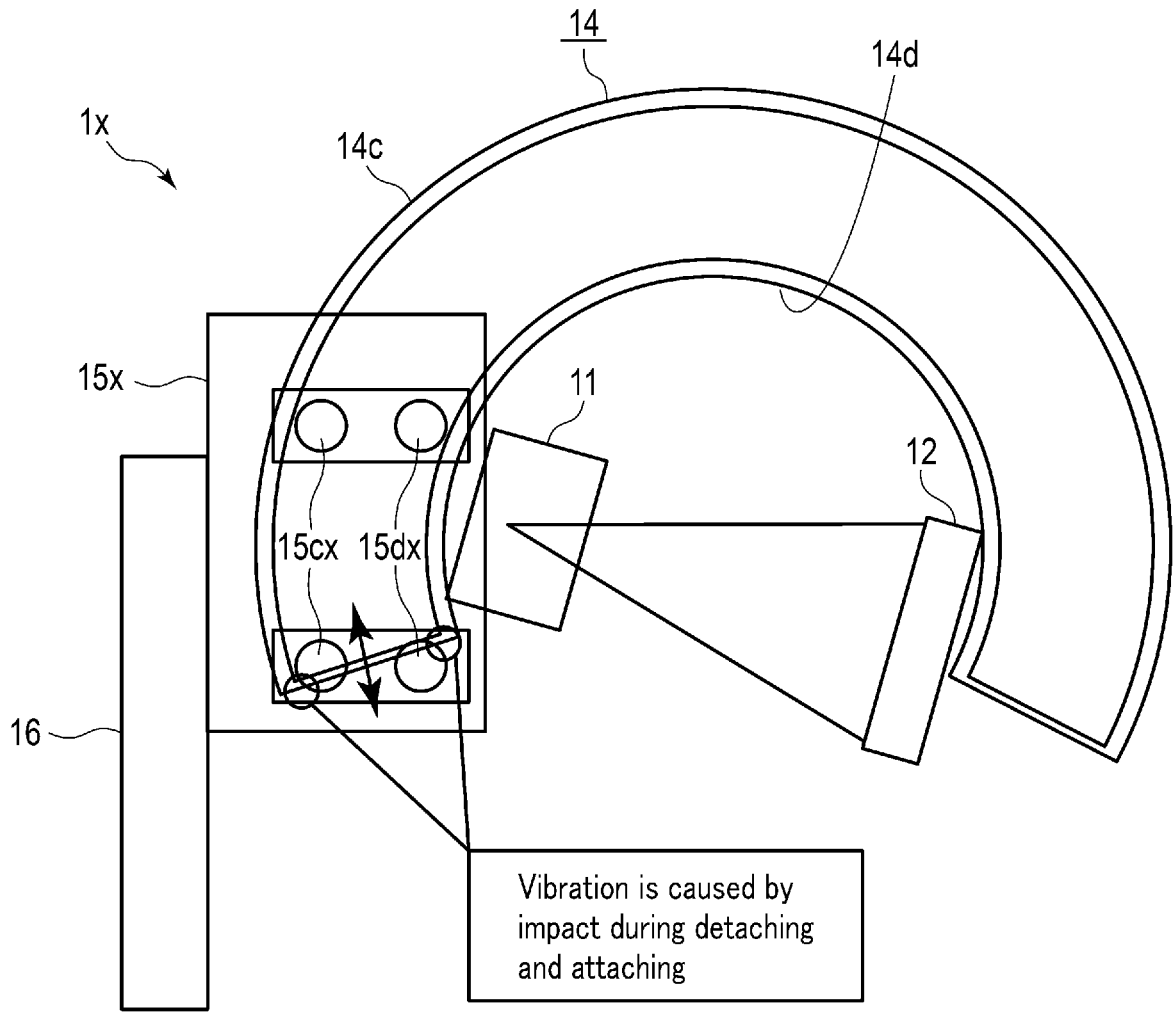
Vibration is caused by impact during detaching and attaching
F I G . 7

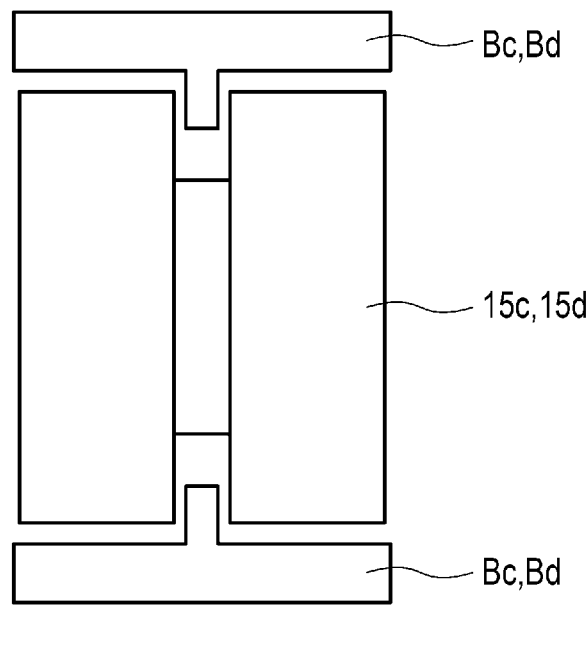
Bc,Bd
15c,15d
Bc,Bd
F I G. 8
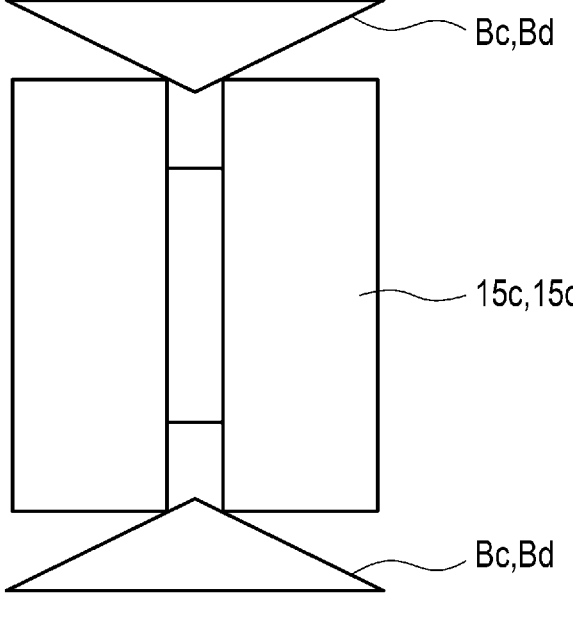
Bc,Bd
15c,15d
Bc,Bd
F I G. 9

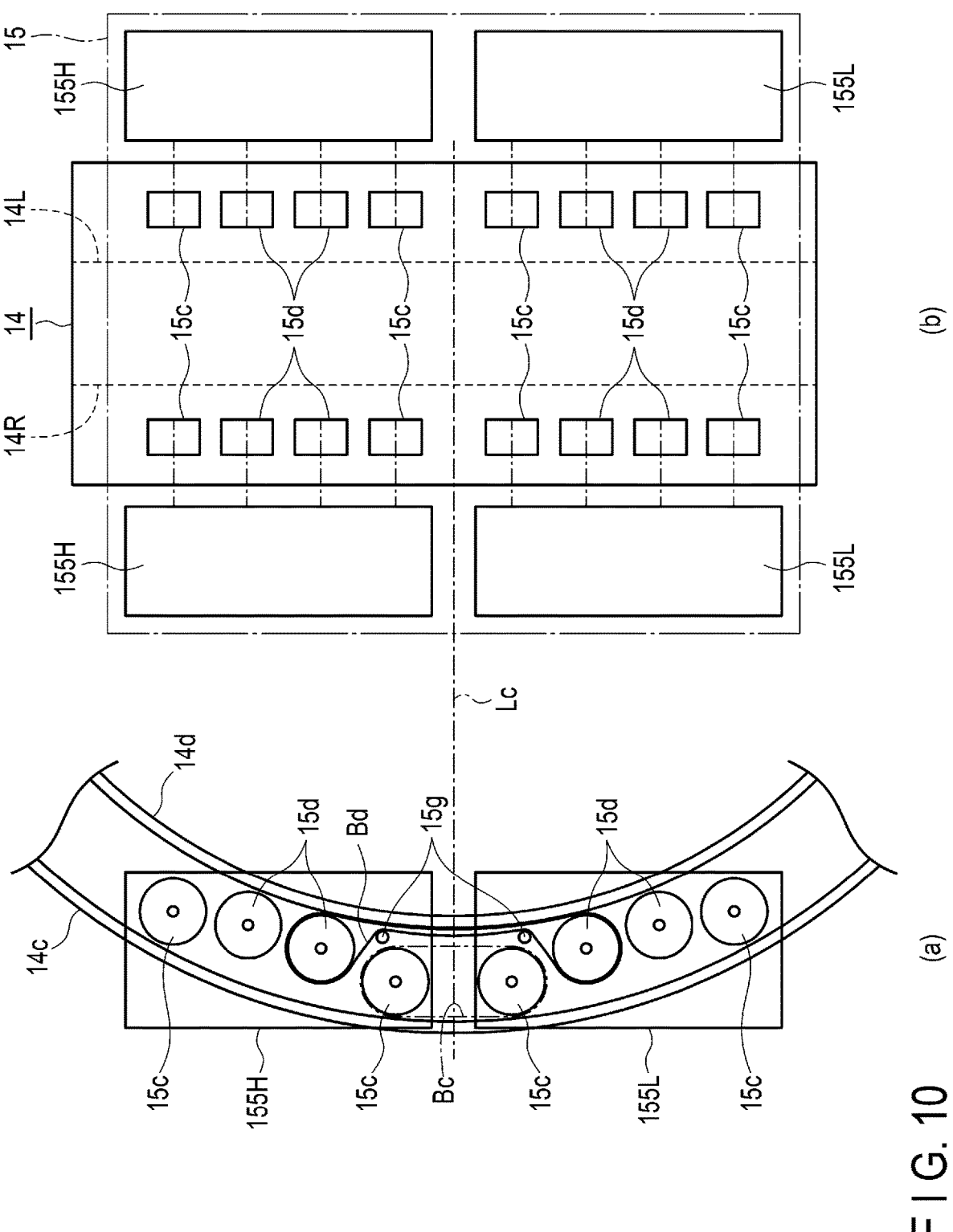
F I G. 10

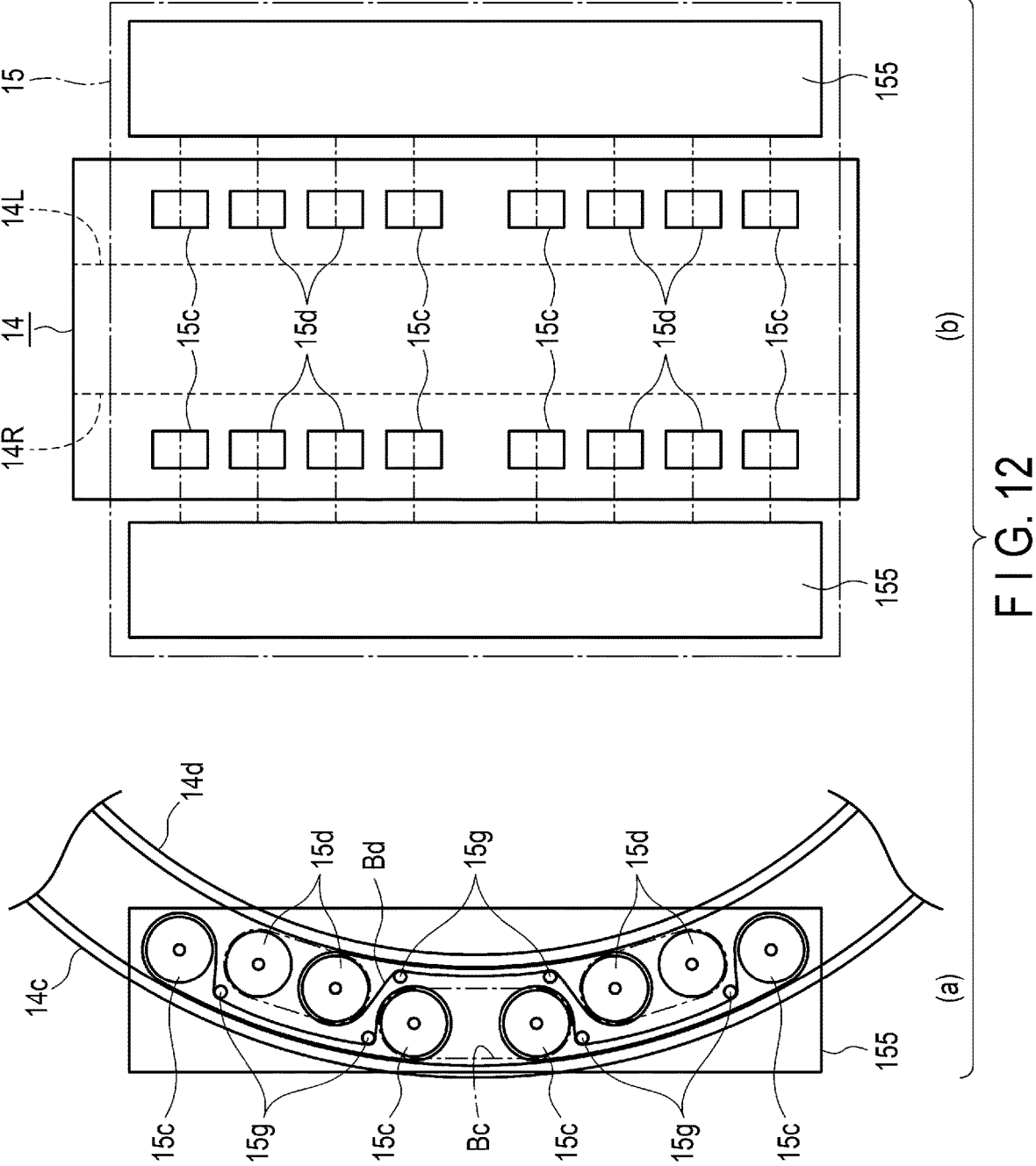
F I G. 12

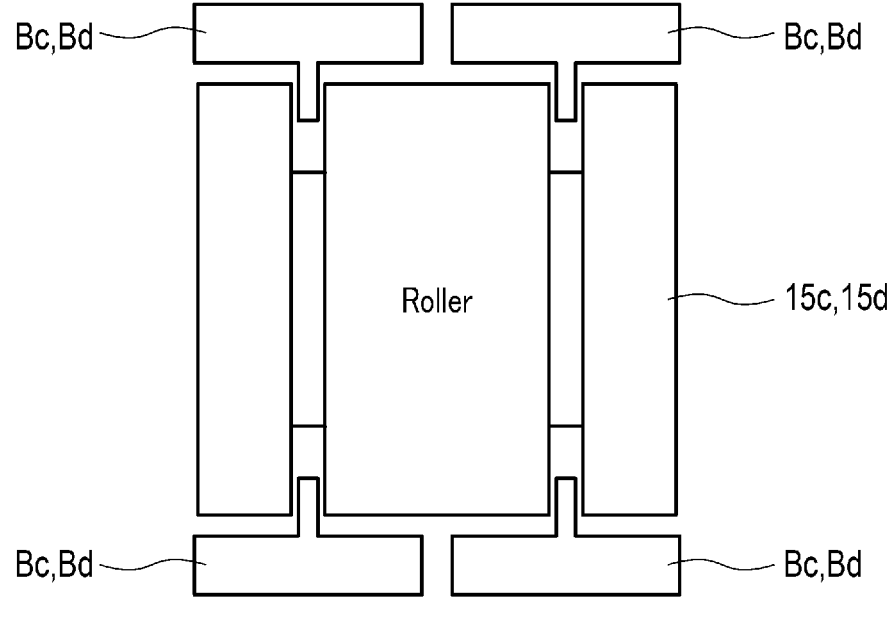
F I G. 13

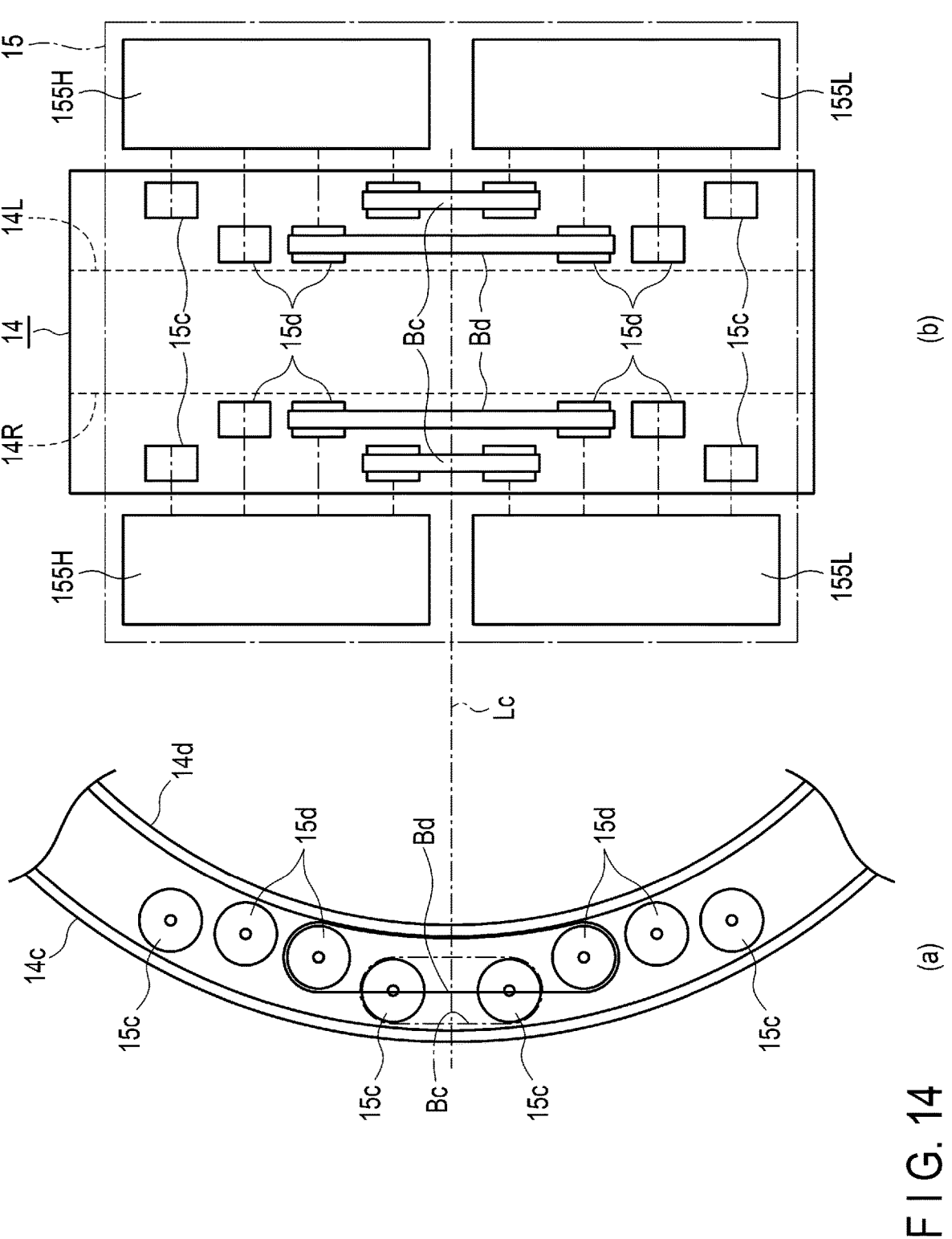
F I G. 14

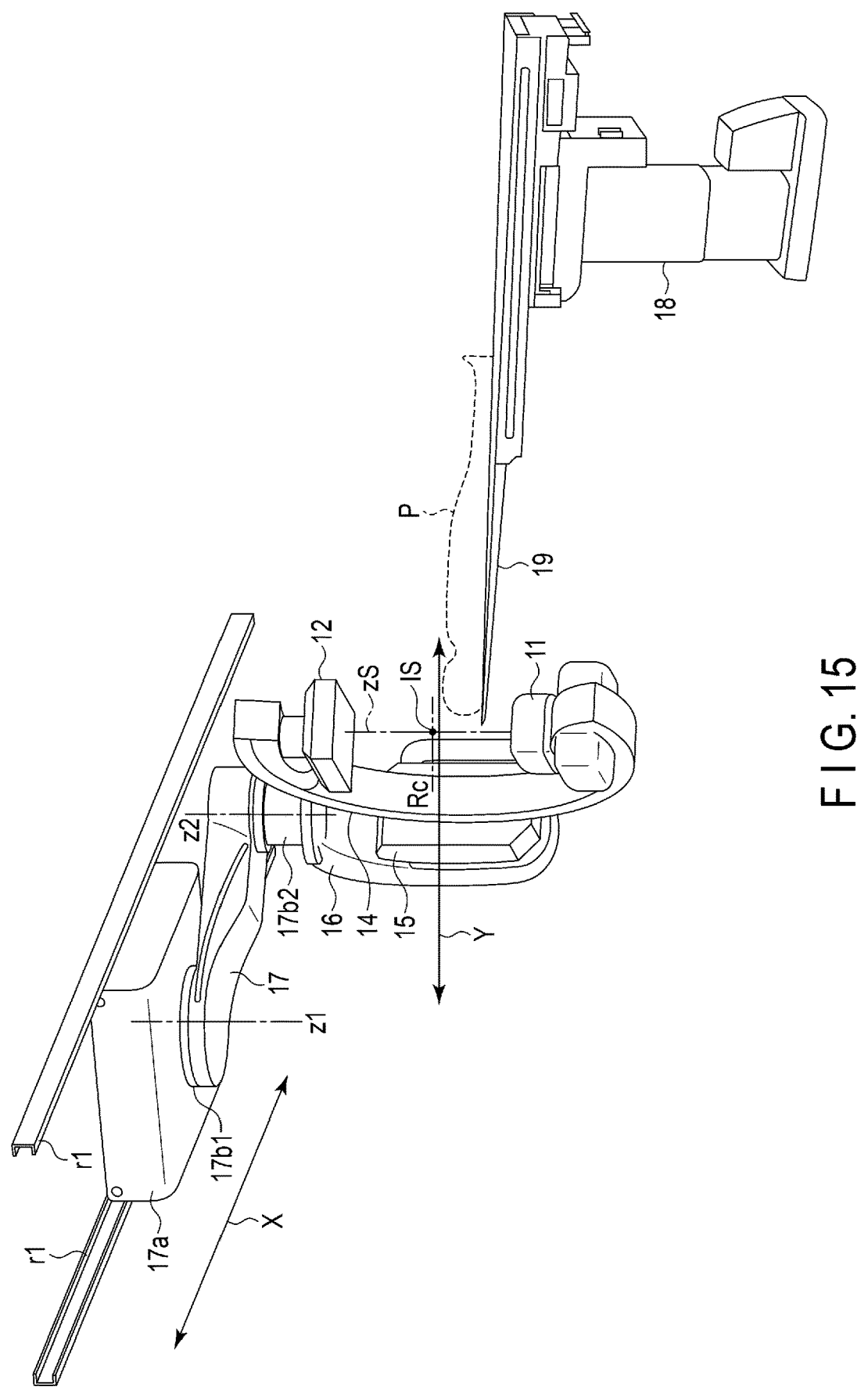
F I G. 15

X-RAY DIAGNOSTIC APPARATUS

CROSS-REFERENCE TO RELATED APPLICATION

This application is based upon and claims the benefit of priority from prior Japanese Patent Application No. 2022-152888, filed Sep. 26, 2022, the entire contents of which are incorporated herein by reference.

FIELD

Embodiments described herein relate generally to an X-ray diagnostic apparatus.

BACKGROUND

An X-ray diagnostic apparatus is an apparatus configured to irradiate a subject mounted on a bed with X-rays from an X-ray source, detect X-rays that have been transmitted through the subject with an X-ray detector, and generate an X-ray image, which is a shadow image proportional to the transmission dose. The X-ray source and the X-ray detector are held by one or more arms, such as a C-arm and/or an Q-arm, so as to face each other.

In such an X-ray diagnostic apparatus, there are cases where, for example, 3D reconstruction is performed, in which X-ray images of a subject are collected by sliding a C-arm within a range of 180° or more, and are reconstructed to generate 3D images. In a catheterization procedure, for example, volume imaging in which X-ray images of an examination site are collected from a range of 180° or more and reconstructed is used. In the case where the examination site is an abdomen area, in particular, since it is difficult to collect images through main rotation based on a positional relationship between the bed and the C-arm, the C-arm needs to be slid to 180° or more.

To ensure a sliding range of 180° or more, some X-ray diagnostic apparatuses are equipped with a double-slide mechanism in which two sliding structures are provided. However, with such a double-slide mechanism, the number of components and the driving units increases, leading to an increase in the cost and an increase in vibration.

On the other hand, in some X-ray diagnostic apparatuses with a single-slide mechanism that slides a C-arm in a range of 180° or more, the C-arm is detached from a part of the sliding mechanism if the angle of sliding has become 180° or more, and the C-arm is attached again at a position where the C-arm has been detached if the angle of sliding should be returned back to the original angle. In such a mechanism, vibration may occur in the C-arm during the detachment and attachment, causing a decrease in image quality of 3D images.

BRIEF DESCRIPTION OF THE DRAWING

FIG. 1 is a schematic diagram showing an example of an outer appearance of an X-ray diagnostic apparatus according to a first embodiment.

FIG. 2 is a schematic diagram for illustrating a configuration of a C-arm and an arm holder as viewed from their sides according to the first embodiment.

FIG. 3 is a cross-sectional view taken along line III-III of FIG. 2.

FIG. 4 is a schematic diagram for illustrating an arrangement of rollers and belts according to the first embodiment.

FIG. 5 is a schematic diagram for illustrating a comparative example of the first embodiment.

FIG. 7 is a schematic diagram for illustrating a comparative example of the first embodiment.

FIG. 8 is a cross-sectional view of rollers and belts for illustrating a modification of the first embodiment.

FIG. 9 is a cross-sectional view of rollers and belts for illustrating another modification of the first embodiment.

FIG. 10 is a schematic diagram for illustrating an arrangement of rollers and belts according to a second embodiment.

FIG. 12 is a schematic diagram for illustrating an arrangement of rollers and belts according to a fourth embodiment.

FIG. 13 is a cross-sectional view of the rollers and belts according to the fourth embodiment.

FIG. 14 is a schematic diagram for illustrating an arrangement of rollers and belts according to a fifth embodiment.

FIG. 15 is a schematic diagram showing an example of an outer appearance of an X-ray diagnostic apparatus according to a modification of each embodiment.

DETAILED DESCRIPTION

Figure 6:
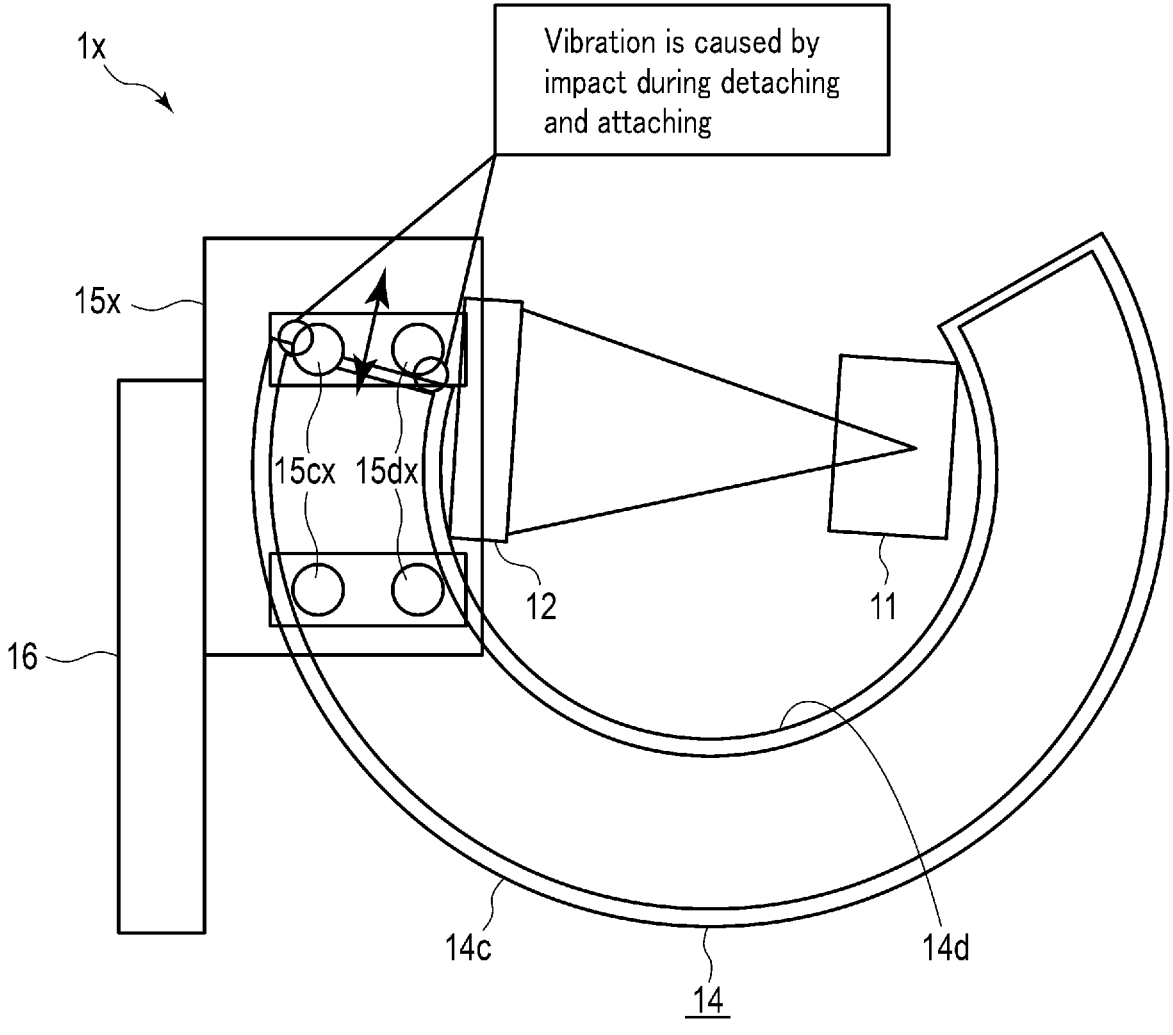
FIG. 6 is a schematic diagram for illustrating a comparative example of the first embodiment.

In general, according to one embodiment, an X-ray diagnostic apparatus comprising: an arm, a pair of grooved portions, a plurality of rollers, and a plurality of belts. The arm is configured to support an X-ray tube at one end and an X-ray detector at another end and has a shape of an arc. The grooved portions are formed on side surfaces of the arm. The plurality of rollers are configured to run in the grooved portions and slidably support the arm along the arc. Each of the belts passes over at least two of the rollers and at least partially abuts on inner walls of the grooved portions.

Hereinafter, an X-ray diagnostic apparatus according to each of the embodiments will be described with reference to the drawings. In the description that follows, a floor-mounted type will be described as a main example of the X-ray diagnostic apparatus; however, the configuration is not limited thereto, and the X-ray diagnostic apparatus may be embodied as a ceiling-suspended type.

First Embodiment

FIG. 1 is a schematic diagram depicting an example of an outer appearance of an X-ray diagnostic apparatus 1 according to the present embodiment. In FIG. 1, the X-ray diagnostic apparatus 1 for circulatory organ diagnosis, on which captured images can be displayed in real time, is shown as an example. In FIG. 1, it is assumed that a body axis direction of the subject 150 is a y-axis, a direction along a pivoting axis z2 of the stand 16 and a rotation axis z1 of the swivel arm 17 is a z-axis, and a direction orthogonal to the y-axis and the z-axis is an x-axis.

The X-ray diagnostic apparatus 1 shown in FIG. 1 includes an X-ray tube 11, an X-ray detector 12, a detector anteroposterior movement part 13, a C-arm 14, an arm holder 15, a stand 16, a swivel arm 17, a bed 18, and a top plate 19.

The X-ray tube 11 is mounted on one end of the C-arm 14. An unillustrated collimator is arranged at a stage prior to the X-ray tube 11. The X-ray tube 11 generates X-rays with which the subject 150 is to be irradiated, using a high voltage supplied from an unillustrated high-voltage generator. The collimator restricts an irradiation range of X-rays generated in the X-ray tube 11 by rotating a diaphragm or opening and closing blades.

The X-ray detector 12 is attached to the detector anteroposterior movement part 13 so as to face the X-ray tube 11. The X-ray detector 12 is realized by, for example, a flat panel detector in which a plurality of X-ray detection semiconductor elements are two-dimensionally arrayed. The X-ray detector 12 detects X-rays that have been transmitted through the subject 150.

The detector anteroposterior movement part 13 is mounted on the other end portion of the C-arm 14. The detector anteroposterior movement part 13 is attached to the C-arm 14 so as to be movable backward and forward along a direction toward the X-ray tube 11.

The C-arm 14 holds the X-ray tube 11 and the detector anteroposterior movement part 13 in such a manner that the X-ray tube 11 and the X-ray detector 12 directly face each other. The C-arm 14 is an example of an arm configured to support the X-ray tube 11 at one end and the X-ray detector 12 at the other end and having the shape of an arc. The C-arm 14 is held by the stand 16 via the arm holder 15.

The arm holder 15 slidably holds the C-arm 14 with respect to a direction of the arc of the C-arm 14, namely, the direction of an arrow a shown in FIG. 1. The arm holder 15 is attached to the stand 16 so as to be pivotable around a rotation axis Rc, which is orthogonal to the pivoting axis z2 of the stand 16, for example, in a direction of an arrow b. In accordance with the pivoting of the arm holder 15 in the b direction, the C-arm 14 also pivots in the b direction. The pivoting of the arm holder 15 in the b direction will be referred to as "main rotation".

The stand 16 is attached to the swivel arm 17 so as to be pivotable around the pivoting axis z2. The stand 16 supports the arm holder 15 in a direction orthogonal to the pivoting axis z2.

The swivel arm 17 is attached, at one end portion, to a floor surface so as to be swivelable around the rotation axis z1. The swivel arm 17 supports the stand 16 at the other end portion.

The stand 16 and the swivel arm 17 are an example of a supporting arm configured, at one end, to support the arm holder 15 to allow its rotation around a rotation axis Rc, which is approximately horizontal, and provided, at the other end, on the floor surface so as to be swivelable around the rotation axis z1, which is approximately vertical. Specifically, the supporting arm includes both a first arm and a second arm. The swivel arm 17 is an example of a first arm provided, at one end, on the floor surface so as to be swivelable around a first rotation axis z1, which is approximately vertical. The stand 16 is an example of the second arm configured to rotatably support the arm holder 15 and supported at the other end of the first arm so as to be rotatable around a second rotation axis z2, which is approximately vertical.

The bed 18 includes a horizontal movement mechanism for horizontally moving the top plate 19 on which the subject 150 is mounted in the body axis direction (y-axis direction), and a vertical movement mechanism for moving the top plate 19 in the vertical direction (z-axis direction).

Next, the C-arm 14 and the arm holder 15 will be described. FIG. 2 is a side view depicting an example of a partial configuration of the C-arm 14 and the arm holder 15 shown in FIG. 1.

As shown in FIG. 2, the C-arm 14 has the shape of an arc. The X-ray detector 12 and the X-ray tube 11 are attached to a first end portion 14a and a second end portion 14b, respectively, of the C-arm 14 so as to directly face each other. A timing belt 141 is stretched along an outer circumferential surface 14c of the C-arm 14, except for a portion passing over a timing belt driving pulley 153.

The arm holder 15 shown in FIG. 2 includes a slide drive mechanism configured to slide the C-arm 14 in the direction shown by the arrow a in FIG. 1 and a slide guide mechanism configured to guide sliding of the C-arm 14. The slide drive mechanism of the arm holder 15 includes, for example, timing belt rollers 151 and 152, a timing belt driving pulley 153, a sliding power transmission key 154, and a power source (e.g., a motor, a servo amplifier, etc.) as well as an unillustrated power transmission mechanism (e.g., a deceleration mechanism).

The timing belt rollers 151 and 152 are provided so as to interpose a portion of the timing belt 141 passing over the timing belt driving pulley 153 on a movement path during a sliding operation. The timing belt rollers 151 and 152 press the timing belt 141 against an outer circumferential surface 14c. The timing belt rollers 151 and 152 are pivotably supported via an unillustrated supporting mechanism included in the slide drive mechanism.

The timing belt driving pulley 153 is provided at a position distanced from the C-arm 14 by a predetermined distance. Teeth are provided over the entire peripheral surface of the timing belt driving pulley 153 at a pitch that allows for meshing with the teeth of the timing belt 141. The sliding power transmission key 154 is a rotation axis of the timing belt driving pulley 153, and is rotationally driven by power transmitted from a power source via a power transmission mechanism. The timing belt driving pulley 153 rotates through the rotational driving of the sliding power transmission key 154. Through the rotation of the timing belt driving pulley 153, the timing belt 141 is carried toward the rotation direction.

At the first end portion 14a of the C-arm 14, an arc-shaped guide block (guide portion) 142 for tucking the timing belt 141 into the side of the inner circumferential surface 14d from the side of the outer circumferential surface 14c is provided. The arc-shaped guide block 142 has the shape of a semicircular column.

On the outer circumferential surface 14c of the C-arm 14, a belt extension portion 144 is formed so as to be approximately flush with an arc surface of the arc-shaped guide block 142, as shown in FIG. 3. The belt extension portion 144 is formed, for example, to have a width equivalent to that of the timing belt 141. The timing belt 141 is provided on the belt extension portion 144.

The C-arm 14 is formed in such a manner that an inner hollow portion is provided therein. The timing belt 141 tucked into the side of the inner circumferential surface 14d from the side of the outer circumferential surface 14c by the arc-shaped guide block 142 is fixed by a fixing part 146 provided in the hollow portion.

At the second end portion 14b of the C-arm 14, an idler pulley 147 for tucking the timing belt 141 from the side of the outer circumferential surface 14c into the side of the inner circumferential surface 14d is provided. The idler pulley 147 is pivotably supported, for example, by a rotation axis.

The tension of the timing belt 141 tucked from the side of the outer circumferential surface 14c into the side of the inner circumferential surface 14d by the idler pulley 147 is adjustably fixed by a tension adjustably fixing part 148. The tension adjustably fixing part 148 is, for example, provided in a hollow portion of the C-arm 14. If the tension of the timing belt 141 need not be adjusted, an arc-shaped guide block 142 may be provided instead of the idler pulley 147, and a fixing part 146 may be provided instead of the tension adjustably fixing part 148.

On the other hand, the slide guide mechanism of the arm holder 15 includes, as shown in FIGS. 2 to 4, for example, grooved portions 14R and 14L, a plurality of rollers (15*d* and 15*c*), a plurality of belts (Bd and Bc), and a plurality of guide rollers 15*g*. FIG. 4(*a*) schematically shows an arrangement of the rollers and the belts from a side surface direction of the C-arm 14, and FIG. 4(*b*) schematically shows an arrangement of the rollers from a front direction of the C-arm 14. That is, FIGS. 4(*a*) and (*b*) schematically show an arrangement of the rollers from directions that are orthogonal to one another. With the plurality of belts (Bd and Bc) and the plurality of rollers (15*d* and 15*c*), the arm holder 15 slidably holds the C-arm 14.

The grooved portions 14R and 14L are formed on side surfaces of the C-arm 14 positioned between the outer circumferential surface 14*c* and the inner circumferential surface 14*d* of the C-arm 14, as shown in FIGS. 3 and 4.

The plurality of rollers (15*d* and 15*c*) run in the grooved portions 14R and 14L and slidably support the C-arm 14 along the arc of the C-arm 14, as shown in FIG. 4. The plurality of rollers include a plurality of inner rollers 15*d* and a plurality of outer rollers 15*c*. The inner rollers 15*d* run on the inner circumferential side of the arc of the C-arm 14 in the grooved portions 14R and 14L. The outer rollers 15*c* run on the outer circumferential side of the arc of the C-arm 14 in the grooved portions 14R and 14L. Each of the inner rollers 15*d* and the outer rollers 15*c* is rotatably provided in a plurality of roller units 155, as shown in FIG. 4(*b*). The number of each of the inner rollers 15*d* and the outer rollers 15*c* is not limited to the illustrated number, and may be freely set.

Each of the roller units 155 is provided in the arm holder 15 so as to face the grooved portions 14R and 14L on the side surface of the C-arm 14, and slidably interposes the C-arm by inserting the inner rollers 15*d* and the outer rollers 15*c* in the grooved portions 14L and 14R.

Each of the belts (Bd and Bc) passes over at least two of the rollers, and at least partially abuts on the inner walls of the grooved portions 14R and 14L. Such belts include an inner belt Bd and an outer belt Bc. The inner belt Bd passes over at least two of the inner rollers 15*d*. The outer belt Bc passes over at least two of the outer rollers 15*c*. The inner belt Bd passes over all the inner rollers 15*d* shown in FIG. 4(*a*). Similarly, the outer belt Bc passes over all the outer rollers 15*c*. It is to be noted that a single belt never passes over both of the inner rollers 15*d* and the outer rollers 15*c*.

The guide rollers 15*g* correct a path of at least one of the inner belt Bd and the outer belt Bc in such a manner that the inner belt Bd and the outer belt Bc are distanced from one another. Four of the six guide rollers 15*g* shown in FIG. 4(*a*) correct the path of the outer belt Bc, and the remaining two guide rollers 15*g* correct the path of the inner belt Bd. Each of the guide rollers 15*g* has a smaller diameter than the inner belt Bd and the outer belt Bc.

Next, effects achieved by the above-described configuration will be described.

It is assumed that, with the slide drive mechanism, the arc-shaped C-arm 14 slides along its arc.

In the slide guide mechanism, as shown in FIG. 4(*a*), the inner belt Bd passing over the inner rollers 15*d* and the guide rollers 15*g* run, in the grooved portions 14R and 14L formed on the side walls of the C-arm 14, together with the inner rollers 15*d* and the guide rollers 15*g*, while contacting the inner walls of the grooved portions 14R and 14L. If, for example, the C-arm 14 slides in a downward direction as viewed in the drawing, the inner belt Bd and the inner rollers 15*d* run so as to rotate in a clockwise direction as viewed in the drawing. If, for example, the C-arm 14 slides in an upward direction as viewed in the drawing, the inner belt Bd and the inner rollers 15*d* run so as to rotate in a counterclockwise direction as viewed in the drawing.

Similarly, the outer belt Bc passing over the outer rollers 15*c* and the guide rollers 15*g* run together with the outer rollers 15*c* and the guide rollers 15*g*, while contacting the inner walls of the grooved portions 14R and 14L. If, for example, the C-arm 14 slides in a downward direction as viewed in the drawing, the outer belt Bc and the outer rollers 15*c* run so as to rotate in a counterclockwise direction as viewed in the drawing. If, for example, the C-arm 14 slides in an upward direction as viewed in the drawing, the outer belt Bc and the outer rollers 15*c* run so as to rotate in a clockwise direction as viewed in the drawing.

It is to be noted that, since the inner rollers 15*d* and the outer rollers 15*c* rotate in opposite directions during the sliding of the C-arm 14, a single belt never passes over both of the inner rollers 15*d* and the outer rollers 15*c*.

The inner belt Bd runs in the grooved portions 14R and 14L of the C-arm 14 while contacting the inner wall on the side of the inner circumferential surface 14*d*, and the outer belt Bc runs in contact with the inner wall on the side of the outer circumferential surface 14*c*. Accordingly, even if the C-arm 14 is detached from or attached to a part of the slide guide mechanism, since the inner belt Bd and the outer belt Bc passing over a plurality of rollers mitigate a level difference between the rollers in transmitting power to the C-arm 14, it is possible to reduce vibration of the C-arm 14.

As described above, according to the first embodiment, the X-ray diagnostic apparatus 1 includes a C-arm 14, grooved portions 14R and 14L, a plurality of rollers, and a belt. The C-arm 14 is configured to support an X-ray tube 11 at one end and an X-ray detector 12 at the other end, and has the shape of an arc. The grooved portions 14R and 14L are formed on side surfaces of the C-arm 14. The plurality of rollers run in the grooved portions 14R and 14L, and slidably support the C-arm 14 along its arc. Each of the belts passes over at least two of the rollers, and at least partially abuts on inner walls of the grooved portions 14R and 14L. The belts are thus configured to connect the rollers, allowing the grooved portions 14R and 14L and the rollers to be in contact with one another via the belts. Thereby, the grooved portions 14R and 14L and the rollers are continuously brought into contact with one another via the belts. This allows the belts to be partly in contact with the inner walls of the grooved portions 14R and 14L during sliding of the C-arm 14, thereby suppressing vibration of the C-arm 14 caused by a level difference between the rollers. This allows X-ray images for 3D reconstruction to be collected from an angular range of 180° or more, while suppressing vibration. It is thereby possible to suppress a decrease in image quality in a single slide mechanism.

More specifically, in an X-ray diagnostic apparatus 1*x* according to a comparative example shown in FIG. 5, belts do not pass over a plurality of outer rollers 15*cx* and a plurality of inner rollers 15*dx* included in the arm holder 15*x*, unlike the first embodiment. Accordingly, vibration is caused by an impact at the time of detaching from and attaching to the C-arm 14 in the X-ray diagnostic apparatus 1 according to the comparative example, as shown in FIGS. 6 and 7.

On the other hand, according to the first embodiment, even in the case where the C-arm 14 is detached from or attached to a part of the slide guide mechanism, the inner belt Bd and the outer belt Bc passing over a plurality of rollers mitigate a level difference between the rollers in transmitting power to the C-arm 14. Accordingly, it is possible to reduce vibration of the C-arm 14.

Also, according to the first embodiment, the plurality of rollers include a plurality of inner rollers 15*d* and a plurality of outer rollers 15*c*. The inner rollers 15*d* run on the inner circumferential side of the arc of the C-arm 14 in the grooved portions 14R and 14L. The outer rollers 15*c* run on the outer circumferential side of the arc of the C-arm 14 in the grooved portions 14R and 14L. Such belts include an inner belt Bd and an outer belt Bc. The inner belt Bd passes over at least two of the inner rollers 15*d*. The outer belt Bc passes over at least two of the outer rollers 15*c*. Accordingly, it is possible to slidably support the C-arm 14 on each of the inner circumferential side and the outer circumferential side of the arc, in addition to the above-described effects.

According to the first embodiment, the guide rollers 15*g* correct a path of at least one of the inner belt Bd and the outer belt Bc in such a manner that the inner belt Bd and the outer belt Bc are distanced from one another. Thereby, even if the widths of the grooved portions 14R and 14L are smaller than the sum of the diameters of the inner rollers 15*d* and the diameters of the outer rollers 15*c*, it is possible to avoid a contact between the inner belt Bd and the outer belt Bc by the guide rollers 15*g* correcting the paths of the belts, in addition to the above-described effects. Accordingly, the thickness of the C-arm 14 (widths of the grooved portions 14R and 14L) can be made smaller than the sum of the diameters of the inner rollers 15*d* and the outer rollers 15*c*, thus making it possible to reduce both the size and the weight of the apparatus.

According to the first embodiment, the guide rollers 15*g* have a smaller diameter than the inner rollers 15*d* and the outer rollers 15*c*. Accordingly, it is possible to implement guide rollers 15*g* even in a narrow region in the grooved portions 14R and 14L, such as a region between the inner rollers 15*d* and a region between the outer rollers 15*c*, in addition to the above-described effects.

Modification of First Embodiment

The first embodiment can be modified in the following manner. The modifications can be combined with one another, or with any of the embodiments to be described below.

With respect to the cross-sectional structure of the rollers and the belts, no specific stipulations have been made; however, the configuration is not limited thereto, and specific stipulations may be made. For example, as shown in FIG. 8 or 9, guide grooves may be formed on a circumferential surface of each of the inner rollers 15*d* and the outer rollers 15*c*, which function as the rollers. Each of the inner belt Bd and the outer belt Bc, which function as the belts, may include an engaging portion configured to engage with the guide grooves of the rollers. The engaging portion of each of the inner belt Bd and the outer belt Bc may include a projection, as shown in FIG. 8. Alternatively, the engaging portion of the inner belt Bd and the outer belt Bc may be a top portion of an inverted triangle cross section, as shown in FIG. 9. The shapes of the guide grooves and the engaging portions are not limited to the shapes shown in FIGS. 8 and 9, and any shapes may be used. In either case, with the present modification, it is possible to prevent a lateral displacement of the inner belt Bd and the outer belt Bc, thereby preventing the inner belt Bd and the outer belt Bc from falling off from the rollers, in addition to the above-described effects.

Second Embodiment

FIG. 10 is a schematic diagram for illustrating an arrangement of a plurality of rollers and belts according to a second embodiment, and redundant descriptions will be omitted by assigning the same reference numerals to substantially the same portions as those in FIG. 4. The same applies to the embodiments and the modifications to be described below.

In the second embodiment, some of the rollers are connected via belts, unlike the first embodiment in which all the rollers are connected via belts. In accordance therewith, two roller units 155H and 155L are provided in the second embodiment, in place of a single roller unit 155. Providing the two roller units 155H and 155L is not essential, but can be optionally adopted.

The roller units 155H and 155L have substantially the same configuration in which the above-described roller unit 155 is split in two. Also, each of the roller units 155H and 155L can be, when broken, replaced with a new one independently from the other roller units 155L and 155H.

In accordance therewith, the inner rollers 15*d* are provided in an even number. That is, since each of the roller units 155H and 155L has the same configuration, even if each of the roller units 155H and 155L includes an even number or an odd number of inner rollers 15*d*, the total number of the inner rollers 15*d* becomes an even number. Also, the inner rollers 15*d* over which the inner belt Bd passes are arranged so as to be symmetric with respect to a central line Lc splitting the even number of inner rollers 15*d* in two. In FIG. 10, the inner belt Bd passes over the inner rollers 15*d* across the different roller units 155H and 155L in such a manner that they interlock with one another. That is, the inner belt Bd passes over the inner rollers 15*d* at the lower end of the upper roller units 155H and the inner rollers 15*d* at the upper end of the lower roller units 155L.

Similarly, the outer rollers 15*c* are provided in an even number. The outer rollers 15*c* over which the outer belt Bc passes are arranged so as to be symmetric with respect to a central line Lc splitting an even number of outer rollers 15*c* in two. In FIG. 10, the outer belt Bc passes over the outer rollers 15*c* across the different roller units 155H and 155L in such a manner that they interlock with one another. That is, the outer belt Bc passes over the outer rollers 15*c* at the lower end of the upper roller units 155H and the outer rollers 15*c* at the upper end of the lower roller units 155L.

The other configurations are similar to those of the first embodiment.

Next, effects achieved by the above-described configuration will be described.

It is assumed that, with the slide drive mechanism, the arc-shaped C-arm 14 slides along its arc.

At this time, in the slide guide mechanism, the inner belt Bd passing over the inner rollers 15*d* and the guide rollers 15*g* in the vicinity of the central line Lc run, in the grooved portions 14R and 14L formed on side walls of the C-arm 14, together with the inner rollers 15*d* and the guide rollers 15*g*, while contacting the inner walls of the grooved portions 14R and 14L, as shown in FIG. 10(*a*).

Similarly, the outer belt Bc passing over the outer rollers 15*c* in the vicinity of the central line Lc runs together with the outer rollers 15*c*, while contacting the inner walls of the grooved portions 14R and 14L.

Accordingly, even if an end portion of the C-arm 14 has reached the vicinity of the center of the arm holder 15, since each of the inner belt Bd and the outer belt Bc passing over a plurality of rollers mitigates a level difference between the rollers in transmitting power to the C-arm 14, it is possible to reduce vibration of the C-arm 14. More specifically, in the case where a plurality of roller units 155H and 155L are provided, a distance between adjacent rollers across the different roller units 155H and 155L may be longer than a distance between adjacent rollers in the same roller unit 155H or 155L. Even in such a case, since adjacent rollers across the different roller units 155H and 155L are connected via belts, it is possible to mitigate a level difference between the rollers and to suppress vibration of the C-arm 14. Also, the rollers over which the belt passes are arranged so as to be symmetric with respect to a central line Lc splitting an even number of rollers in two. Accordingly, it is possible to reduce vibration evenly regardless of the sliding direction, without causing a deviation in how the vibration is suppressed among the two roller units 155H and 155L.

As described above, according to the second embodiment, some of the rollers are coupled via belts, unlike the first embodiment in which all the rollers are coupled via belts. Accordingly, it is possible to selectively connect only rollers that vibrate greatly with a belt, in addition to the above-described effects.

Also, according to the second embodiment, an even number of inner rollers 15d are provided. The inner rollers 15d over which the inner belt Bd passes are arranged so as to be symmetric with respect to a central line Lc splitting an even number of inner rollers 15d in two. The outer rollers 15c are provided in an even number. The outer rollers 15c over which the outer belt Bc passes are arranged so as to be symmetric with respect to a central line Lc splitting an even number of outer rollers 15c in two. Accordingly, it is possible to reduce vibration evenly regardless of the sliding direction.

Modification of Second Embodiment

The second embodiment can be modified in the following manner, and can be combined with any of the embodiments to be described below.

In the second embodiment, the inner belt Bd passes over the inner rollers 15d in the vicinity of the center of the arm holder 15, and the outer belt Bc passes over the outer rollers 15c in the vicinity of the center of the arm holder 15; however, the configuration is not limited thereto. For example, the inner belt Bd may pass over the inner rollers 15d in the vicinity of each end portion of the arm holder 15 and the outer belt Bc may pass over the outer rollers 15c in the vicinity of each end portion of the arm holder 15. In this case, it is possible to reduce vibration at the time of detachment and attachment, similarly to the first embodiment, in addition to the effects of the second embodiment.

The inner belt Bd may pass over the inner rollers 15d in the vicinity of the center of the arm holder 15, and the outer belt Bc may pass over the outer rollers 15c in the vicinity of each end portion of the arm holder 15. Alternatively, the outer belt Bc may pass over the outer rollers 15c in the vicinity of the center of the arm holder 15, and the inner belt Bd may pass over the inner rollers 15d in the vicinity of each end portion of the arm holder 15. Even with such modification, it is possible to reduce vibration at the time of detachment and attachment to some degree.

Third Embodiment

Figure 11:
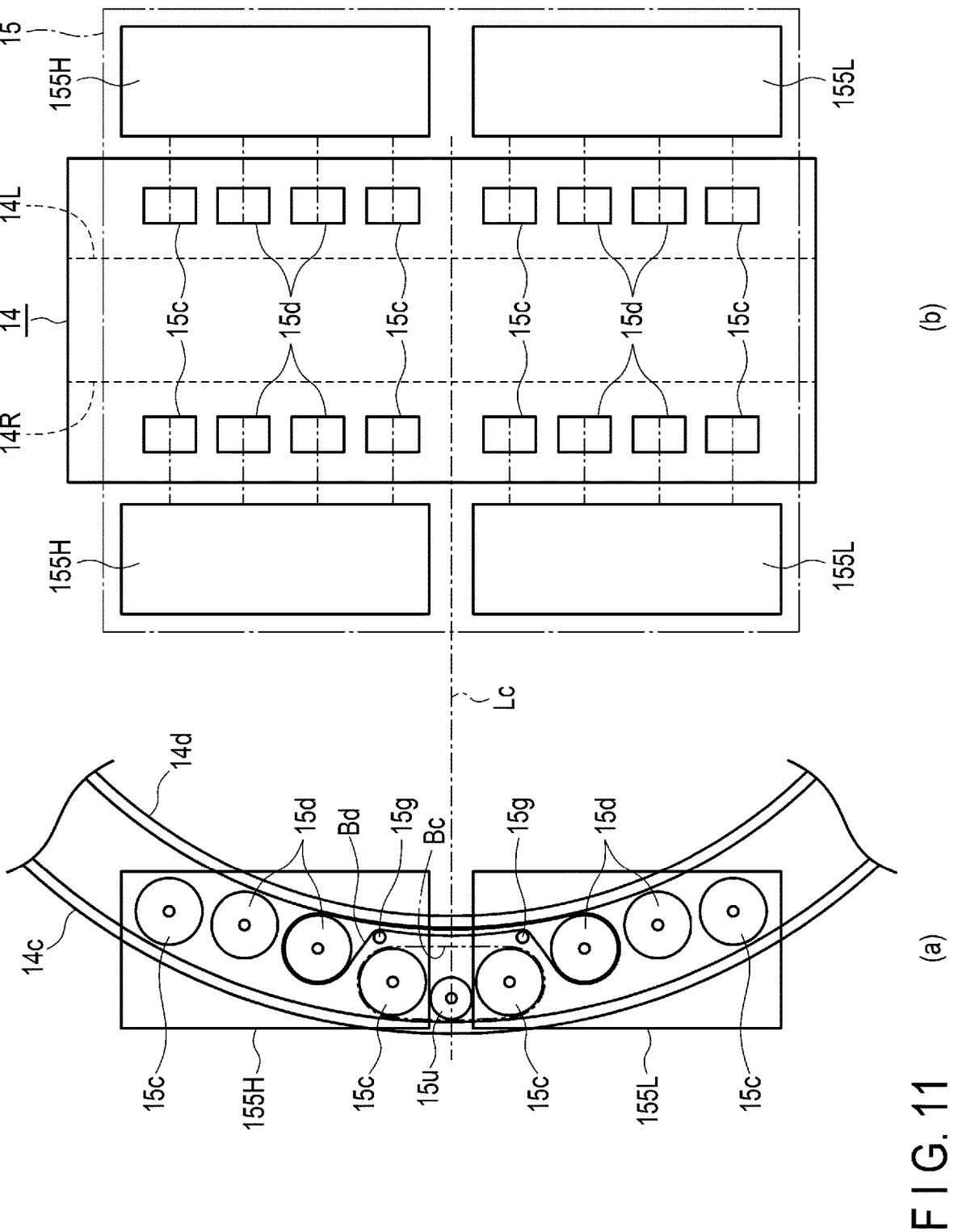
FIG. 11 is a schematic diagram for illustrating an arrangement of rollers and belts according to a third embodiment.

FIG. 11 is a schematic diagram for illustrating an arrangement of rollers and belts according to a third embodiment.

In the third embodiment, an auxiliary roller 15u is added to the configuration of the second embodiment in which the outer rollers 15c in the vicinity of the center are connected via the outer belt Bc.

The auxiliary roller 15u is provided between at least one adjacent pair of the outer rollers 15c over which the outer belt Bc passes, and runs on the outer circumferential side of the arc so as to make the outer belt Bc abut on the inner walls of the grooved portions 14R and 14L.

The other configurations are similar to those of the first embodiment.

With the above-described configuration, since the auxiliary roller 15u runs on the outer circumferential side of the arc so as to make the outer belt Bc abut on the inner walls of the grooved portions 14R and 14L, it is possible to expand an area over which the outer belt Bc contacts the grooved portions 14R and 14L. Accordingly, it is possible to reduce vibration of the C-arm 14 by means of the outer belt Bc contacting the grooved portions 14R and 14L via the auxiliary roller 15u, in addition to the above-described effects.

More specifically, the outer belt Bc couples the outer rollers 15c in the shortest distance, and thus does not contact the grooved portions 14R and 14L at a position distanced from the outer rollers 15c. On the other hand, the auxiliary roller 15u allows the outer belt Bc to abut on the inner walls of the grooved portions 14R and 14L, thereby expanding an area over which the outer belt Bc contacts the grooved portions 14R and 14L. Since the inner belt Bd coupling the inner rollers 15d in the shortest distance contacts the inner walls of the grooved portions 14R and 14L, an auxiliary roller 15u need not be provided for the inner rollers 15d.

The auxiliary roller 15u according to the third embodiment is not necessarily provided on the outer belt Bc in the vicinity of the center, and may be provided on an outer belt Bc at a given position.

Fourth Embodiment

FIG. 12 is a schematic diagram for illustrating an arrangement of a plurality of rollers and belts according to a fourth embodiment, and FIG. 13 is a cross-sectional view of the rollers and belts according to the fourth embodiment.

In the fourth embodiment, all the rollers on each of the inner circumferential side and the outer circumferential side are connected via a plurality of belts, unlike the first embodiment in which all the rollers on each of the inner circumferential side and the outer circumferential side are connected via a single belt.

The inner belt Bd passes over at least one adjacent pair of the plurality of inner rollers 15d. A first guide groove and a second guide groove may be formed on a circumferential surface of each of the inner rollers 15d so as to be distanced from one another. In the case where each inner belt Bd individually passes over at least two pairs of the inner rollers 15d, each inner belt Bd engages with the first guide grooves or the second guide grooves.

The outer belt Bc passes over at least one adjacent pair of the plurality of outer rollers 15c. A first guide groove and a second guide groove are formed on a circumferential surface of each of the outer rollers 15c so as to be distanced from one another. In the case where each outer belt Bc individually passes over at least two pairs of the outer rollers 15c, each outer belt Bc engages with the first guide grooves or the second guide grooves.

The other configurations are similar to those of the first embodiment.

With the above-described configuration in which all the rollers on each of the inner circumferential side and the outer circumferential side are connected via a plurality of belts, even if one of the belts brakes, the other belts will remain working, thus making it possible to continue a sliding operation with no problem, in addition to the above-described effects. This prevents, for example, performing X-ray imaging again, leading to a reduction in exposure.

Fifth Embodiment

FIG. 14 is a schematic diagram for illustrating an arrangement of rollers and belts according to a fifth embodiment.

In the fifth embodiment, unlike the second embodiment in which the inner rollers 15d and the outer rollers 15c are positioned on the same plane, the inner rollers 15d and the outer rollers 15c are positioned on different planes, as shown in FIG. 14(b). Similarly, the outer belt Bc and the inner belt bc are positioned on different planes.

In accordance therewith, the outer belt Bc and the inner belt bc do not contact each other, and the guide rollers 15g can be omitted, as shown in FIG. 14(a).

The other configurations are similar to those of the second embodiment.

With the above-described configuration in which the inner rollers 15d and the outer rollers 15c are positioned on different planes, and the outer belt Bc and the inner belt bc do not contact each other, the guide rollers 15g can be omitted, thereby achieving simplification.

The fifth embodiment may be applied to the configuration of any of the first, third, and fourth embodiments in which the inner rollers 15d and the outer rollers 15c are positioned on the same plane, as well as the configuration of the second embodiment. The same applies to the modifications of the first to fourth embodiments.

In the above-described embodiments, the X-ray diagnostic apparatus 1 has been described as a floor-mounted type, as shown in FIG. 1; however, the configuration is not limited thereto. For example, the X-ray diagnostic apparatus 1 may be embodied as a ceiling-suspended type, as shown in FIG. 15. In FIG. 15, a base 17a is supported by rails r1 provided on a ceiling surface, and is movable along a longitudinal direction (X direction) of the rails r1. This allows the base 17a to move in the horizontal direction. With a fulcrum 17b1 connected to a proximal end of the swivel arm 17, the base 17a rotates around a first rotation axis z1 extending in a vertical direction from the fulcrum 17b1, thereby rotating the swivel arm 17 in a direction horizontal to the ceiling surface. That is, the swivel arm 17 is supported by the base 17a so as to be rotatable around the first rotation axis z1 in the vertical direction. With a fulcrum 17b2 at a distal end of the swivel arm 17 connected to an upper end of the stand 16, the swivel arm 17 rotates around a second rotation axis z2 extending in the vertical direction from the fulcrum 17b2, thereby rotating the stand 16 in a direction horizontal to the ceiling surface. That is, the stand 16 is supported by the swivel arm 17 so as to be rotatable around the second rotation axis Z2 in the vertical direction. The arm holder 15 at a lower end of the stand 16 supports the C-arm 14 in such a manner that the C-arm 14 is slidably movable along its arc shape, and rotatably holds the C-arm 14 around an arm main rotation axis Rc extending parallel to the ceiling surface. In this manner, the C-arm 14 is slidably and rotatably supported by the stand 16.

The stand 16 and the swivel arm 17 are an example of a supporting arm configured, at one end, to support the arm holder 15 to allow its rotation around the rotation axis Rc, which is approximately horizontal, and provided, at the other end, on the ceiling surface so as to be swivelable around the rotation axis z1, which is approximately vertical. Specifically, the supporting arm includes both a first arm and a second arm. The swivel arm 17 is an example of a first arm provided, at one end, on the ceiling surface so as to be swivelable around a first rotation axis z1, which is approximately vertical. The stand 16 is an example of the second arm configured to rotatably support the arm holder 15 and supported at the other end of the first arm so as to be rotatable around a second rotation axis z2, which is approximately vertical.

In the case where the X-ray diagnostic apparatus 1 is configured as a ceiling-suspended type, the supporting arm may be implemented as a swivel support arm in which the stand 16 and the swivel arm 17 are integrally formed, by omitting the second rotation axis z2. The swivel support arm is another example of the supporting arm configured, at one end, to support the arm holder 15 to allow its rotation around a rotation axis Rc, which is approximately horizontal, and provided, at the other end, on the ceiling surface so as to be swivelable around a rotation axis z1, which is approximately vertical. However, the swivel support arm does not include the above-described first arm or the second arm.

According to at least one of the embodiments described above, it is possible to suppress a decrease in image quality in a single slide mechanism.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an arm configured to support an X-ray tube at one end and an X-ray detector at another end, and having a shape of an arc;
a pair of grooved portions formed on side surfaces of the arm;
a plurality of rollers configured to run in the grooved portions and slidably support the arm along the arc; and
a plurality of belts each passing over at least two of the rollers and at least partially abutting on inner walls of the grooved portions.

2. The X-ray diagnostic apparatus according to claim 1, wherein
the plurality of rollers include:
a plurality of inner rollers configured to run on an inner circumferential side of the arc in the grooved portions; and
a plurality of outer rollers configured to run on an outer circumferential side of the arc in the grooved portions, and
the plurality of belts include:
an inner belt passing over at least two of the plurality of inner rollers; and
an outer belt passing over at least two of the plurality of outer rollers.

3. The X-ray diagnostic apparatus according to claim 2, further comprising:

a plurality of guide rollers configured to correct a path of at least one of the inner belt and the outer belt in such a manner that the inner belt and the outer belt are distanced from one another.

4. The X-ray diagnostic apparatus according to claim 3, wherein the guide rollers have a smaller diameter than the inner rollers and the outer rollers.

5. The X-ray diagnostic apparatus according to claim 2, wherein the inner rollers are provided in an even number, and the inner rollers over which the inner belt passes are arranged so as to be symmetric with respect to a central line splitting an even number of inner rollers in two.

6. The X-ray diagnostic apparatus according to claim 2, wherein the outer rollers are provided in an even number, and the outer rollers over which the outer belt passes are arranged so as to be symmetric with respect to a central line splitting an even number of outer rollers in two.

7. The X-ray diagnostic apparatus according to claim 2, further comprising:

an auxiliary roller provided between at least one adjacent pair of the outer rollers over which the outer belt passes, and configured to run on the outer circumferential side of the arc so as to make the outer belt abut on the inner walls of the grooved portions.

8. The X-ray diagnostic apparatus according to claim 2, wherein the inner belt passes over at least one adjacent pair of the plurality of inner rollers, and the outer belt passes over at least one adjacent pair of the plurality of outer rollers.

9. The X-ray diagnostic apparatus according to claim 8, wherein a first guide groove and a second guide groove are formed on a circumferential surface of each of the inner rollers so as to be distanced from each other, and when each inner belt individually passes over at least two pairs of the inner rollers, each inner belt engages with a plurality of the first guide grooves or a plurality of the second guide grooves.

10. The X-ray diagnostic apparatus according to claim 8, wherein a first guide groove and a second guide groove are formed on a circumferential surface of each of the outer rollers so as to be distanced from one another, and when each outer belt individually passes over at least two pairs of the outer rollers, each outer belt engages with a plurality of the first guide grooves or a plurality of the second guide grooves.

11. The X-ray diagnostic apparatus according to claim 1, wherein a guide groove is formed on a circumferential surface of each of the rollers, and each of the belts includes an engaging portion engaging with the guide groove.

12. The X-ray diagnostic apparatus according to claim 1, further comprising:

an arm holder including the belts and the rollers and configured to slidably hold the arm; and a supporting arm configured, at one end, to support the arm holder to allow its rotation around a rotation axis, which is approximately horizontal, and provided, at another end, on a floor surface or a ceiling surface so as to be swivelable around a rotation axis, the rotation axis being approximately vertical.

13. The X-ray diagnostic apparatus according to claim 12, wherein the supporting arm includes:

a first arm provided, at one end, on a floor surface or a ceiling surface so as to be swivelable around a first rotation axis, which is approximately vertical; and a second arm configured to rotatably support the arm holder and supported at another end of the first arm so as to be rotatable around a second rotation axis, which is approximately vertical.

14. The X-ray apparatus according to claim 1, wherein the grooved portions and the at least two of the rollers are continuously brought into contact with one another via the plurality of belts.

\*   \*   \*   \*   \*